United States Patent [19]

Zoche

[11] Patent Number: 4,925,964
[45] Date of Patent: May 15, 1990

[54] PROCESS FOR THE MANUFACTURE OF KETOXIMOSILANES

[75] Inventor: Günter Zoche, Bonn, Fed. Rep. of Germany

[73] Assignee: Huels Aktiengesellschaft, Mar, Fed. Rep. of Germany

[21] Appl. No.: 432,509

[22] Filed: Nov. 7, 1989

[30] Foreign Application Priority Data

Nov. 17, 1988 [DE] Fed. Rep. of Germany ....... 3838897

[51] Int. Cl.$^5$ ............................................... C07F 7/10
[52] U.S. Cl. ................................................... 556/422
[58] Field of Search ........................................ 556/422

[56] References Cited

U.S. PATENT DOCUMENTS

| 3,448,136 | 6/1969 | Paude et al. | 556/422 X |
| 3,697,568 | 10/1972 | Boissieras et al. | 556/422 |
| 4,033,991 | 7/1977 | Shinohara et al. | 556/422 X |
| 4,380,660 | 4/1983 | Mathew et al. | 556/422 |

Primary Examiner—Paul F. Shaver
Attorney, Agent, or Firm—Felfe & Lynch

[57] ABSTRACT

Ketoximosilanes are prepared by reacting alkyl- or alkenyl-acetoxysilanes with ketoximes in the presence of an amine, followed by isolation of the ketoximosilanes by separation of the liquid phases. The ketoximosilane products are useful as cross-linking agents for organopolysiloxane compositions.

2 Claims, No Drawings

PROCESS FOR THE MANUFACTURE OF KETOXIMOSILANES

FIELD OF THE INVENTION

This invention relates to a novel process for the preparation of ketoximosilanes. These silicon compounds are particularly useful as cross-linking silicon compounds for the manufacture of compositions which are storable under exclusion of water and, upon exposure to moisture at room temperature, harden into elastomers. Such compositions are obtained by admixing diorganopolysiloxanes having condensable terminal groups and cross-linking silicon compounds.

BACKGROUND OF THE INVENTION AND THE PRIOR ART

It is known to prepare ketoximosilanes by reacting alkyltrichlorosilanes with ketoximes; see, for example, German Auslegeschrift No. 1 301 140, published European Application No. 0 082 324, Soviet Pat. No. 435 243 and Soviet Pat. No. 724 514. The performance of these processes always involves the risk that the ketoxime and ketoximosilane come in contact with inorganic substances of a strong acid nature. The resulting intermediate hydrogen chloride then forms the hydrochloride of the ketoxime. For example, methylethylketoxime boils under normal pressure at 152° C. without decomposing, whereas the hydrochloride thereof vigorous decomposes at 50° to 70° C. Such decompositions, moreover, can be triggered by catalytic amounts of $FeCl_3$, for example. Under such conditions, ketoximosilanes also tend to undergo explosive decompositions. L. J. Tyler reports on two violent explosions of this type in *Chemical Engineering News*, 52 (1974) 35, 3.

It is also known to prepare ketoximosilanes by reacting organosilanes with ketoximes in the presence of suitable acid acceptors and solvents; see, for example, U.S. Pat. Nos. 3,962,160, 3,441,583, 3,341,486, 3,817,909, German Auslegeschrift No. 1 301 140, German Auslegeschrift No. 1 255 924, French Pat. No. 1,118,495, European Pat. No. 0 036 262, and W. Noll, *Chemie und Technologie der Silikone*, page 342, published by Verlag Chemie, Weinheim 1968).

In these known processes, solid ammonium salts such as ammonium chloride or amine hydrochlorides are obtained as by-products, depending upon the type of acid acceptor which is used. These salts necessarily precipitate during the reaction in the form of a crystalline slurry. Once the reaction has gone to completion, the resulting oximosilane is separated from the precipitated salt, and subsequently the salt is washed again with large amounts of solvent. Since it is not possible to economically wash these salts such that they are absolutely clean, they introduce the disadvantage that they adsorb on their surface a significant amount of the desired end product, namely oximosilane.

The filtrate contains the desired oximosilane which remains in the sump after distilling of the solvent. A subsequent distillation of the particular ketoximosilane must be carried out in a vacuum, which is expensive and not without danger, because this process step already approaches the limit of thermostability of the ketoximosilane.

OBJECT OF THE INVENTION

It is an object of the present invention to provide a method for preparing ketoximosilanes which excludes the risk of decompositions or explosions, does not produce solid substances which have to be separated, and does not require any distillation of the ketoximosilane product.

Other objects and advantages of the invention will become apparent as the description thereof proceeds.

DESCRIPTION OF THE INVENTION

I have discovered that the above object is achieved by a process for the preparation of a ketoximosilane of the formula

$$(R_1)_n Si[O-N=C(R_2)_2]_{(4-n)} \quad (I),$$

wherein $R_1$ is alkyl of 1–18 carbon atoms or alkenyl of 2–18 carbon atoms,
n is an integer from 0 to 3 inclusive, and
$R_2$ are identical or different alkyls of 1 to 6 carbon atoms, which comprises reacting an acetoxysilane of the formula:

$$(R_1)_n Si[OCOCH_3]_{(4-n)} \quad (II),$$

wherein $R_1$ and n have the meanings previously defined, with a ketoxime of the formula

$$HO-N=C(R_2)_2 \quad (III).$$

wherein $R_2$ has the meanings previously defined. In this process an aliphatic amine which forms with the liberated acetic acid an adduct which is liquid below +40° C. is added to the reaction mixture. In order to separate the liquid adduct, a volatile, inert organic solvent in which the product of the formula I is soluble is added. After separation of the adduct phase, the desired end product of the formula I is recovered from the solvent phase by evaporation of the solvent.

Examples of suitable aliphatic amines are isopropylamine, isobutylamine, secondary butylamine, trimethylamine and triethylamine. It is known that these amines form anhydrous acetic acid adducts which are liquid at room temperature. The molar composition (amine : acetic acid) of these adducts is in most cases smaller than 1. The reaction of amine and acetic acid to form the adduct is exothermic.

In accordance with the present invention, a separate adduct phase is in some cases also obtained without the addition of a solvent. However, the separation of the solvent-free phases is difficult, because they are viscous and of similar density. Examples of suitable solvents are pentane, hexane, heptane, cyclohexane and 1,1,2-trichloro-1,2,2,-trifluoro-ethane. Only the adducts are sparsely soluble in these solvents, so that after addition of the solvent two easily separable liquid phases form immediately. The ketoximosilanes can be readily isolated from the separated solvent phase by distilling of the solvent. In contrast to other known processes, such as those described in published European Application No. 0 273 189 and German Pat. No. 37 03 484, the process according to the present invention yields the ketoximosilanes as colorless substances without distillation in a vacuum.

The following examples illustrate the present invention and will enable others skilled in the art to understand it more completely. It should be understood, however, that the invention is not limited solely to the particular examples given below.

EXAMPLE 1

Vinyl-tri-(ethyl-methyl-ketoximo)-silane

While stirring, 232 g (1 mol) of vinyl-triacetoxy-silane and 274 g (3.15 mols) of ethyl-methyl-ketoxime were combined in a 2-liter flask. While cooling, 146 g (2 mols) of secondary butyl amine were gradually added at a rate which assured that the temperature of the flask contents did not rise above +30° C. The two oily phases which were formed were difficult to separate, and for this reason 1000 ml of pentane were added. The rapidly separating liquid phases were separated at 22° C. The pentane was distilled out of the lighter weight phase at normal pressure. Residual amounts of pentane were removed at a sump temperature of about 80° C. at a pressure of 1 mbar. Vinyl-tris-(ethyl-methylketoximo)-silane remained behind as a clear, virtually colorless liquid.

EXAMPLE 2

Methyl-tris-(ethyl-methyl-ketoximo)-silane

While stirring, 1,200 ml of hexane, 220 g (1 mol) of methyltriacetoxy-silane, and 274 g (3.15 mols) of ethyl-methyl-ketoxime were combined in a 2-liter flask. Subsequently, while cooling, 101 g (1 mol) of triethylamine were gradually added to the reaction mixture at a rate so that the temperature of the flask contents did not exceed +40° C. The two rapidly separating phases were separated at 22° C. The hexane was distilled out of the lighter weight phase at normal pressure. Residual hexane was drawn off at a sump temperature of about 80° C. at 1 mbar. Methyltris-(ethyl-methyl-ketoximo)-silane remained behind as a clear, colorless liquid.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. In the method of preparing a ketoximosilane of the formula $$(R_1)_n Si[O-N=C(R_2)_2]_{(4-n)} \qquad (I),$$

wherein $R_1$ is alkyl of 1 to 18 carbon atoms or alkenyl of 2 to 18 carbon atoms, n is an integer from 0 to 3, inclusive, $R_2$ are identical or different alkyls of 1 to 6 carbon atoms, by reacting an acetoxysilane of the formula $$(R_1)_n Si[OCOCH_3]_{(4-n)} \qquad (II),$$

wherein $R_1$ and n have the meanings previously defined, with a ketoxime of the formula $$HO-N=C(R_2)_2 \qquad (III).$$

wherein $R_2$ has the meanings previously defined, which releases acetic acid, the improvement which comprises adding to the reaction mixture an aliphatic amine which forms with the released acetic acid an adduct which is liquid below +40° C., and isolating the ketoximosilane from the resulting 2-phase liquid system by separation of the adduct phase.

2. The method of claim 1 wherein the liquid phases are separated by adding a volatile inert organic solvent to the system, and distilling the solvent out of the solvent phase after the phase separation.

* * * * *